US006271256B1

(12) United States Patent
Berkowitz et al.

(10) Patent No.: US 6,271,256 B1
(45) Date of Patent: Aug. 7, 2001

(54) METHODS FOR CONTROLLING GRAM NEGATIVE BACTERIA IN MAMMALS WITH BICYCLO SPIROETHER COMPOUNDS

(75) Inventors: Barry Berkowitz, Framingham, MA (US); George Sachs, Encino, CA (US); Chris Blackburn, Natick, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/451,622

(22) Filed: Nov. 30, 1999

Related U.S. Application Data

(62) Division of application No. 08/905,985, filed on Aug. 5, 1997, now Pat. No. 6,017,950.

(51) Int. Cl.[7] ........................ A61K 31/35; A61K 31/415; A61K 33/24

(52) U.S. Cl. ........................ 514/460; 514/393; 514/394; 514/925; 424/653

(58) Field of Search .................................. 514/460, 393, 514/394, 925; 424/653

(56) References Cited

U.S. PATENT DOCUMENTS

| | | | |
|---|---|---|---|
| 3,577,531 | 5/1971 | Gorman et al. | 424/122 |
| 3,719,753 | 3/1973 | Berger | 424/122 |
| 3,839,447 | 10/1974 | Swiger et al. | 260/562 P |
| 3,873,715 | 3/1975 | Pressman et al. | 424/283 |
| 4,302,450 | 11/1981 | Comai et al. | 424/181 |
| 4,751,315 | 6/1988 | Cullen et al. | 549/415 |
| 5,229,380 | 7/1993 | Harris | 514/152 |
| 5,618,564 | 4/1997 | Kimura et al. | 424/653 |
| 5,629,297 | 5/1997 | McColm | 514/29 |

FOREIGN PATENT DOCUMENTS

| | | |
|---|---|---|
| 356192 | 2/1990 | (WO). |
| 655246 | 5/1995 | (WO). |
| WO 96/05204 | 2/1996 | (WO). |
| WO 96/24341 | 8/1996 | (WO). |
| WO 96/24342 | 8/1996 | (WO). |

OTHER PUBLICATIONS

Berge, Stephen M. et al., "Pharmaceutical Salts", *Journal of Pharmaceutical Sciences*, 66:1–19 (1977).

Blaser, M.J., "*Helicobacter pylori*: microbiology of a 'slow' bacterial infection", *Trends in Microbiology*, 1:255–260 (1993).

Borén, T. et al., "Attachment of *Helicobacter pylori* to Human Gastric Epithelium Mediated by Blood Group Antigens", *Science*, 262:1892–1895 (1993).

Dick–Hegedus, E. and Lee, A., "Use of a Mouse Model to Examine Anti–*Helicobacter pylori* Agents", *Scand. J. Gastroenterol.*, 26:909–915 (1991).

Eaton, K.A. et al., "Essential Role of Urease in Pathogenesis of Gastritis Induced by *Helicobacter pylori* in Gnotobiotic Piglets", *Infection and Immunity*, 59:2470–2475 (1991).

Evans, D.G. et al., "Cloning, Nucleotide Sequence, and Expression of a Gene Encoding an Adhesin Subunit Protein of *Helicobacter pylori*", *Journal of Bacteriology*, 175:674–683 (1993).

Falk, P. et al., "An in vitro adherence assay reveals that *Helicobacter pylori* exhibits cell lineage–specific tropism in the human gastric epithelium", *Proc. Natl. Acad. Sci. USA*, 90:2035–2039 (1993).

Ferrero, R.L. and Lee, A., "The Importance of Urease in Acid Protection for the Gastric–clonising Bacteria *Helicobacter pylori* and *Helicobacter felis* sp. nov.", *Microbial Ecology in Health and Disease*, 4:121–134 (1991).

Haas,, R. et al., "Aflagellated mutants of *Helicobacter pylori* generated by genetic transformation of naturally competent strains using transposon shuttle mutagenesis", *Molecular Microbiology*, 8(4):753–760; Vac A (1993).

Hazell, S.L. et al., "*Campylobacter pyloridis* and Gastritis: Association with Intracellular Spaces and Adaption to an Environment of Mucus as Important Factors in Colonization of the Gastric Epithelium," *The Journal of Infectious Diseases*, 153:658–663 (1986).

Hopkins R.J. and Morris, J.G. "*Helicobacter pylori*: The Missing Link in Perspective", *The American Journal of Medicine*, 97:265–277 (1994).

Huesca, M. et al., "Therapeutics Used to Alleviate Peptic Ulcers Inhibit *H. pylori* Receptor Binding in vitro", *Zbl. Bakt.*, 280:244–252 (1993).

Hunt, R.H., "*Helicobacter Pylori*; From Theory to Practice", *The American Journal of Medicine*, 100(5A):5A–1S–5A–60S (1996).

(List continued on next page.)

Primary Examiner—Kevin E. Weddington
(74) Attorney, Agent, or Firm—Lahive & Cockfield, LLP; Giulio A. DeConti, Jr.; Elizabeth A. Hanley

(57) ABSTRACT

Methods for controlling growth of gram negative bacteria, such as *Helicobacter pylori*, which are agents associated with disorders of the gastrointestinal tract of a mammal are described. They include administering a therapeutically effective amount of a polyether ionophore antibiotic to a mammal, such that growth of gram negative bacteria which are agents associated with disorders of the gastrointestinal tract of a mammal is controlled. Packaged pharmaceutical compositions for controlling gram negative bacteria are also described. The packaged compositions include a container holding a therapeutically effective amount of a pharmaceutical composition for controlling gram negative bacteria which are agents associated with disorders of the gastrointestinal tract of a mammal and instructions for using the pharmaceutical composition for control of the gram negative bacteria, such that growth of gram negative bacteria which are agents associated with disorders of the gastrointestinal tract of a mammal is controlled. The pharmaceutical composition includes at least one polyether ionophore antibiotic or a bicyclic spiroether.

20 Claims, No Drawings

OTHER PUBLICATIONS

Labigne, A. et al., "Shuttle Cloning and Nucleotide Sequences of *Helicobacter pylori* Genes Responsible for Urease Activity," *Journal of Bacteriology*. 173:1920–1931 (1991).

Leying, H. et al., "Cloning and genetic characterization of a *Helicobacter pylori* flagellin gene", *Molecular Microbiology*, 6(19):2863–2874 (1992).

Malfertheiner, P. and Dominguez–Munoz, J.E., "Rationale for Eradication of *Helicobacter pylori* Infection in Duodenal Ulcer Disease", *Clinical Therapeutics*, 15 Supp. B:37–48 (1993).

Marshall, B.J. et al., "Original isolation of *Campylobacter pyloridis* from human gastric mucosa", *Microbios Letters*, 25:83–88 (1984).

Matin, A. et al., "Capacity of *Helicobacter pylori* To Generate Ionic Gradients at Low pH is Similar to That of Bacteria Which Grow under Strongly Acidic Conditions", *Infection and Immunity*. 64:1434–1436 (1996).

Mobley, H.L. "Defining *Helicobacter pylori* as a Pathogen: Strain heterogeneity and Virulence", *The American Journal of Medicine*, 100:5A–2S–5A–64S (1996).

Morehead, M.C. et al., "Some growth and metabolic characteristics of monensin–sensitive and monensin–resistant strains of prevotella ruminicola," *Appl. Environ. Microbiol.*, 58:1617–1623, (1992).

Nagata, K. et al., "Inhibitory Action of Lansoprazole and its Analogs against *Helicobacter pylori*; Inhibition of Growth Is Not Related to Inhibition of Urease", *Antimicrobial Agents and Chemotherapy*, 39:567–570 (1995).

Rathbone, et al., "*Campylobacter pyloridis*—A. new factor in peptic ulcer disease?", *Gut*, 27:635–641 (1986).

Sachs, G. et al., "Gastric Acid Secretion: Activation and Inhibition", *Yale Journal of Biology and Medicine*, 67:81–95 (1994).

Schmitt, W. and Haas, R., "Genetic analysis of the *Helicobacter pylori* vacuolating cytotoxin: structural similarities with the IgA protease type of exported protein", *Molecular Microbiology*, 12(2):307–319 (1994).

Skrivanova, V. et al., "The effect of monensin on performance and selected biochemical and hematological parameters in the blood of calves," *Database Medline*, Acc.No. 93182329 veterinarni medicina, (1992).

Taylor, D.N. and Blaser, M.J., "The Epidemiology of *Helicobacter pylori* Infection", *Epidemiologic Review*, 13:42–50 (1991).

Trifonov, L.S. and Orahovats, A.S., "Intramolecular Cyclizatinos of Allenic Acylureas and ~ amides", *Helvetica Chimica Acta* 70:262–270, (1987).

Tsukube, H. and Sohmiya, H., "Chiral Recognition of Asymmetric Amine Salts by Chemically Modified Polyether Antibiotics", *J. Org. Chem.*, 56:875–878, (1991).

Warren, J.R. and Marshall, B., "Unidentified Curved Bacilli on Gastric Epithelium in Active Chronic Gastritis", *The Lancet*, 1:1273–1276 (1983).

METHODS FOR CONTROLLING GRAM NEGATIVE BACTERIA IN MAMMALS WITH BICYCLO SPIROETHER COMPOUNDS

This application is a divisional application of Ser. No. 08/905,985 filed of Aug. 5, 1997 now U.S. Pat. No. 6,017,950, Allowed. The contents of all of the aforementioned application(s) are hereby incorporated by reference.

BACKGROUND

*Helicobacter pylori* bacterial infections are a serious problem in humans. They have been shown to be a strong causative factor in gastric ulcer disease, such as stomach ulcers and small intestine ulcers which can result in death. *Helicobacter pylori* is a gram-negative, S-shaped, microaerophilic bacterium that was discovered and cultured from a human gastric biopsy specimen. (Warren, J. R. and B. Marshall, (1983) Lancet 1: 1273–1275; and Marshall et al., (1984) *Microbios Lett.* 25: 83–88). *H. pylori* bacterial cells can survive in a low pH environment because of an enzyme on their outer cell wall called urease. Urease converts urea in the stomach into bicarbonate and ammonia. The bicarbonate and ammonia neutralize the acid gastric juices, thereby providing a protective layer around the *H. pylori*.

Since *H. pylori* are gram-negative rod type bacteria, it is difficult to treat *H. pylori* infections without using agents that will also affect other gram-negative bacteria elsewhere in the body. *H. pylori* has been strongly linked to chronic gastritis and duodenal ulcer disease. (Rathbone et. al., (1986) Gut 27: 635–641). Moreover, evidence is accumulating for an etiologic role of *H. pylori* in nonulcer dyspepsia, gastric ulcer disease, and gastric adenocarcinoma. (Blaser M. J., (1993) *Trends Microbiol.* 1: 255–260). Transmission of the bacteria occurs via the oral route, and the risk of infection increases with age. (Taylor, D. N. and M. J. Blaser, (1991) *Epidemiol. Rev* 13: 42–50). *H. pylori* colonizes the human gastric mucosa, establishing an infection that usually persists for decades. Infection by *H. pylori* is prevalent worldwide. Developed countries have infection rates over 50% of the adult population, while developing countries have infection rates reaching 90% of the adults over the age of 20. (Hopkins R. J. and J. G. Morris (1994) *Am. J. Med.* 97: 265–277).

The bacterial factors necessary for colonization of the gastric environment, and for virulence of this pathogen, are poorly understood. Examples of the putative virulence factors include the following: urease, an enzyme that may play a role in neutralizing gastric acid pH (Eaton et al., (1991) *Infect. Immunol.* 59: 2470–2475; Ferrero, R. L. and A. Lee (1991) *Microb. Ecol. Hlth. Dis.* 4: 121–134; Labigne et al., (1991) *J. Bacteriol.* 173: 1920–1931); the bacterial flagellar proteins responsible for motility across the mucous layer (Hazell et al., (1986) *J. Inf. Dis.* 153: 658–663; Leying et al., (1992) *Mol. Microbiol.* 6: 2863–2874; and Haas et al., (1993) *Mol. Microbiol.* 8: 753–760; Vac A), a bacterial toxin that induces the formation of intracellular vacuoles in epithelial cells (Schmitt, W. and R. Haas, (1994) *Molecular Microbiol.* 12(2: 307–319) and several gastric tissue-specific adhesions (Boren et al., (1993) *Science* 262: 1892–1895; Evans et al., (1993) *J. Bacteriol.* 175: 674–683; and Falk et al., (1993) *Proc. Natl. Acad. Sci.* USA 90: 2035–2039).

Certain therapeutic agents are known to eradicate *H. pylori* infections in vitro. (Huesca et. al., (1993) *Zbl. Bakt.* 280: 244–252; Hopkins, R. J. and J. G. Morris, supra). However, many agents are suboptimally effective in vivo because of bacterial resistance, altered drug distribution, patient non-compliance, poor drug availability and lack of selectivity for *H. pylori*. (Hopkins, R. J. and J. G. Morris, supra). Treatment with antibiotics combined with bismuth are part of a standard regime used to treat *H. pylori* infection. (Malfertheiner, P. and J. E. Dominguez-Munoz (1993) *Clinical Therapeutics* 15 Supp. B: 37–48). Recently, combinations of a proton pump inhibitor and a single antibiotic have been shown to ameliorate duodenal ulcer disease. (Malfertheiner, P. and J. E. Dominguez-Munoz supra).

SUMMARY OF THE INVENTION

This invention provides methods of controlling gram negative bacteria and/or treating gram negative infections. In some embodiments, the methods involve the use of a polyether ionophore antibiotic to selectively control or kill such bacteria. In a preferred method, the gram negative bacteria is associated with gastric *Helicobacter pylori* infections.

The present invention provides various methods for controlling gram negative bacteria, such as *Helicobacter pylori*, by administering to a mammal a therapeutically effective amount of a polyether ionophore antibiotic such that gram negative bacteria in the mammal is controlled.

Polyether ionophore antibiotics useful for controlling gram negative bacteria in a mammal include monensin, nigericin and calcimycin and pharmaceutically acceptable salts or esters thereof. Preferred polyether antibiotics of the invention include those having the formula

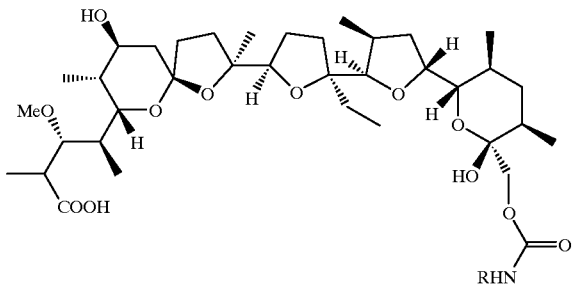

wherein, R is either phenyl, pyridyl or aminoethyl-Fmoc (fluorenylmethoxycarbonyl). Coadministration of proton pump inhibitors, acid agonists or blockers, acid antagonists, bismuth salts or combinations thereof with polyether ionophore antibiotics of the invention is particularly preferred.

The present invention also provides methods for controlling gram negative bacteria in a mammal by administering to a mammal a therapeutically effective amount of a bicyclo spiroether compound having at least one heterocyclic moiety attached to at least one of the ether rings, such that gram negative bacteria in the mammal is controlled.

The present invention provides methods for controlling gram negative bacteria in a mammal by administering to a mammal a therapeutically effective amount of a compound having the formula:

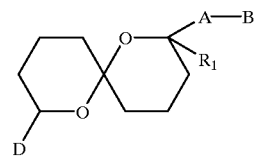

-continued or

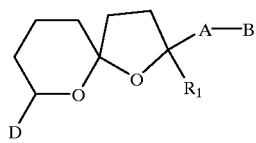

or such that gram negative bacteria in the mammal is controlled. $R_1$ is a hydrogen atom or a substituted or unsubstituted alkyl group and A is either a covalent bond connecting the cyclic ring to B or a substituted or unsubstituted alkylene diradical connecting the cyclic ring to B. B is a heterocyclic group, preferably a tetrahydrofuranyl group, and D is a substituted or unsubstituted alkyl group. The methylene carbon atoms of the cyclic rings are each independently substituted at one or more positions with one or two substitutents selected from hydrogen atoms, hydroxyl groups or substituted or unsubstituted alkyl groups. The methine carbon atoms are each independently substituted with hydrogen atoms or substituted or unsubstituted alkyl groups.

The present invention further provides methods for treating a state characterized by the presence of gram negative bacteria in a mammal. In one embodiment, the method includes administering to a mammal a therapeutically effective amount of a polyether ionophore antibiotic, such that a state characterized by the presence of gram negative bacteria in the mammal is treated. In a preferred embodiment, the gram negative bacteria is *Helicobacter pylori*.

In another embodiment, a method includes administering to a mammal a therapeutically effective amount of a bicyclo spiroether compound having at least one heterocyclic moiety attached to at least one of the ether rings, such that a state characterized by the presence of gram negative bacteria, such as *Helicobacter pylori* in the mammal is treated. The polyether ionophore antibiotics and bicyclo spiroether compounds of the invention are useful for both prophylactic and/or therapeutic treatments of gram negative bacteria found in the gastrointestinal tract of a mammal.

In still another embodiment, a method includes administering to a mammal a therapeutically effective amount of compound having the formula:

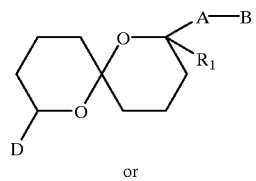

or

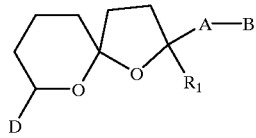

such that a state characterized by the presence of gram negative bacteria, such as *Helicobacter pylori*, in the mammal is treated. A, B, D and $R_1$ are as defined supra.

The present invention provides methods for controlling *Helicobacter pylori* in a mammal. In one embodiment, a method includes administering to a mammal a therapeutically effective amount of a polyether ionophore antibiotic, such that *Helicobacter pylori* in the mammal is controlled.

In another embodiment, a method includes administering to a mammal a therapeutically effective amount of a bicyclo spiroether compound having at least one heterocyclic moiety attached to at least one of the ether rings, such that *Helicobacter pylori* in the mammal is controlled.

In still another embodiment, a method includes administering to a mammal a therapeutically effective amount of a compound having the formula:

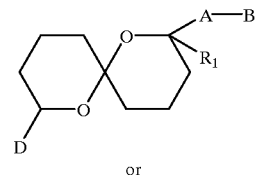

or

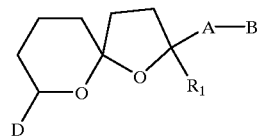

and $R_1$ are as defined supra, such that *Helicobacter pylori* in the mammal is controlled.

The present invention further provides methods for treating a gastrointestinal disorder in a mammal characterized by having gram negative bacteria, such as *Helicobacter pylori*, as a causative agent. In one embodiment, a method includes administration of a therapeutically effective amount of a polyether ionophore antibiotic to a mammal, such that a gastrointestinal disorder characterized by having *Helicobacter pylori* as a causative agent is treated.

In another embodiment, a method includes administering to a mammal a therapeutically effective amount of a bicyclo spiroether compound having at least one heterocyclic moiety attached to at least one of the ether rings, such that a gastrointestinal disorder characterized by having *Helicobacter pylori* as a causative agent is treated.

In still another embodiment, a method includes administering to a mammal a therapeutically effective amount of a compound having the formula:

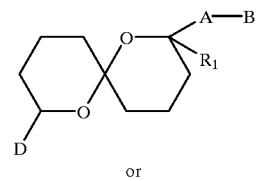

or

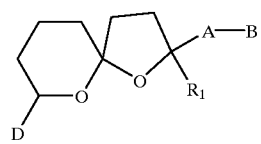

wherein A, B, D and $R_1$ are defined supra, such that a gastrointestinal disorder characterized by having *Helicobacter pylori* as a causative agent is treated.

The present invention also provides methods for treating an ulcer in the gastrointestinal tract of a mammal. In one embodiment, the method includes administration of a therapeutically effective amount of a polyether ionophore antibiotic to a mammal, such that an ulcer of the gastrointestinal tract of the mammal is treated.

The present invention also provides methods for treating an ulcer associated with Helicobacter pyloriin a mammal. In one embodiment, a method includes administering to a mammal a therapeutically effective amount of a polyether ionophore antibiotic, such that an ulcer associated with *Helicobacter pylori* in the mammal is treated.

In another embodiment, a method includes administering to a mammal a therapeutically effective amount of a bicyclo spiroether compound having at least one heterocyclic moiety attached to at least one of the ether rings, such that an ulcer associated with *Helicobacter pylori* in the mammal is treated.

In still another embodiment, the method includes administering to a mammal a therapeutically effective amount of a compound having the formula:

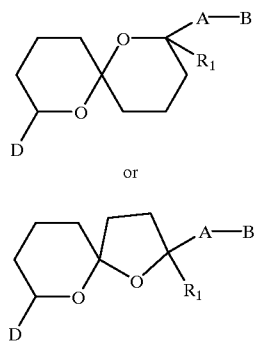

wherein A, B, D and $R_1$ are defined supra, such that an ulcer associated with *Helicobacter pylori* in the mammal is treated.

The present invention also provides packaged pharmaceutical compositions for controlling gram negative bacteria. The container holds a therapeutically effective amount of a pharmaceutical composition for controlling gram negative bacteria in a mammal and instructions for using the pharmaceutical composition for control of the gram negative bacteria. The pharmaceutical composition includes at least one polyether ionophore antibiotic, such that growth of gram negative bacteria in a mammal is treated.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention pertains to a method for controlling gram negative bacteria in a mammal, e.g. control of the growth of gram negative bacteria. One embodiment includes administering to a mammal a therapeutically effective amount of a polyether ionophore antibiotic, such that gram negative bacteria in the mammal is controlled, e.g., gram negative bacteria associated with disorders of the gastrointestinal tract of a mammal. Preferred polyether ionophore antibiotics useful for controlling gram negative bacteria in a mammal include monensin, nigericin and calcimycin and pharmaceutically acceptable salts or esters thereof. Particularly preferred polyether antibiotics of the invention include those having the formula

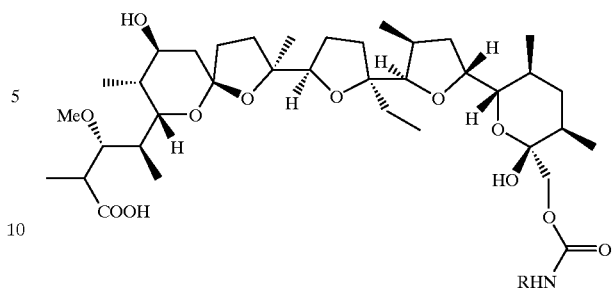

wherein, R is either phenyl, pyridyl or aminoethyl-Fmoc (fluorenylmethoxycarbonyl) and pharmaceutically acceptable salts or esters thereof. Coadministration of proton pump inhibitors (PPIs), acid agonists or blockers, bismuth salts or combinations thereof with polyether ionophore antibiotics of the invention is particularly preferred.

In certain embodiments of the invention, the following polyether ionophore compounds are excluded from use in the method of the invention: salinomycin, ionomycin, lasalocid and the benzylated carboxylic acid of monensin.

The language "controlling gram negative bacteria" is intended to include changes in growth or replication of the gram negative bacteria or eradication of gram negative bacteria. The language includes preventing survival or inhibiting continued growth and replication of gram negative bacteria. In a preferred embodiment, the control of the gram negative bacteria is such that a gram negative bacterial infection is treated. In a preferred embodiment, the control is selective such that a particular target gram negative bacteria is controlled while other bacteria which is not detrimental to the mammal is allowed to remain substantially uncontrolled or substantially unaffected, e.g. gram positive bacteria.

The term "gram negative bacteria" is art recognized and is intended to include those bacteria which, when treated with either gentian violet, or its analog crystal violet, followed by iodine and an organic wash do not stain. Typically, a counterstain of some contrasting color is applied to demonstrate gram negative bacteria. The preferred gram negative bacteria are those capable of growing or existing in the gastrointestinal tract of mammals which can be problematic under some conditions. In one embodiment, preferred gram negative bacteria is of the genus Helicobacter, more preferably the species *Helicobacter pylori*.

The term "gastrointestinal tract" is art recognized and is intended to include the digestive system of an animal. The gastrointestinal tract(s) includes the esophagus, stomach and intestine, e.g., small and large.

The language "grain negative bacteria which are agents associated with disorders of the gastrointestinal tract" is intended to include those gram negative bacteria which cause or are associated with disorders of the gastrointestinal tract, including inflammation and/or ulcers. Disorders of the gastrointestinal tract also include those symptoms not manifested by the presence of ulcerations in the gastric mucosa, such as gastritis, non-ulcer dyspepsia, esophageal reflux disease and peptic ulcer disease. *Helicobacter pylori* is an example of a gram negative bacteria which is associated with disorders of the gastrointestinal tract as described previously. Additionally, *Helicobacter pylori* can be associated with mucosa associated lymphoid tissue (MALT) acne rosacea, Gulf Veteran's Syndrome, Chronic Fatigue Syndrome and halitosis. In one embodiment, gram negative bacteria normally found as flora in the gastrointestinal tract, which do not cause disorders of the gastrointestinal tract under normal circumstances, e.g., E. coli., are not encompassed by this terminology.

The term "mammal," as used herein, refers to an animal, more preferably a warm-blooded animal, most preferably cattle, sheep, pigs, horses, dogs, cats, rats, mice, and humans. Mammals susceptible to infection by gram negative bacteria, e.g., Helicobacter pylori, or susceptible to disorders of the gastrointestinal tract are included as part of this invention.

The term "therapeutically effective amount" is that amount necessary or sufficient to control gram negative bacteria in the above methods, e.g., prevent or reduce the gram negative bacteria's ability to grow. The term "therapeutically effective amount" also can be that amount necessary to eradicate, e.g., kill, the gram negative bacteria. An effective amount of the therapeutic agent necessary to control gram negative bacteria can vary according to factors such as the type of gram negative bacteria, the amount of gram negative bacteria already present in the animal, the age, sex, and weight of the animal, and the ability of the compounds of the present invention to control gram negative bacterial in the mammal. Dependent upon the desired outcome, the amount of control can be tailored for structure/relationship correlations of the therapeutic agents.

A therapeutically effective amount preferably controls the amount of gram negative bacteria and/or a disease state characterized by the presence of gram negative bacteria in the infected mammal by at least about 20%, more preferably by at least about 40%, even more preferably by at least about 60%, and still more preferably by at least about 80% relative to untreated subjects. These percentages refer to a decrease in the amount of gram negative bacteria found in the infected animal and/or the decrease in symptoms associated with a disease state characterized by the presence of gram negative bacteria in the infected animal relative to untreated subjects. For example, a sample of gastric juices can be obtained from an animal infected with gram negative bacteria and treated with one of the compounds described supra. A second sample of gastric juices can be obtained from an animal also infected with gram negative bacteria which is left untreated with any compound. One skilled in the art would be able to develop the samples on a petri dish (as described in the Examples infra) to determine whether the compound tested controlled the gram negative bacteria relative to the untreated sample, e.g., reduction or elimination of colonies relative to the untreated sample. Furthermore, the ability of a compound of the invention to control gram negative bacteria associated with disorders of the gastrointestinal tract of a mammal can be evaluated in an animal model system or by standard in vitro assays that may be predictive of efficacy in treating gram negative bacteria associated with infection of the gastrointestinal tract in human diseases. Such in vivo model systems include those described by E. Dick-Hegedus & A. Lee, Scand. J. Gastroenterol. 26, 909 (1991).

The term "polyether ionophore antibiotic" is art recognized and is described in detail in U.S. Pat. Nos. 4,302,450; 3,839,447; 3,719,753; 3,577,531; and 3,873,715, all of which are incorporated herein by reference. Furthermore, the biology and chemistry of the polyether ionophore antibiotics are disclosed in Polyether Antibiotics-Naturally Occurring Acid Ionophores, Volume 1—Biology, edited by John W. Westley. Westley, Marcel Dekker, Inc. 1982, ISBNO-9247-1655-8 (v. 1) and Polyether Antibiotics—Naturally Occurring Acid Ionophores, Volume 2—Chemistry, Edited by John W. Westley, Marcel Dekker, Inc., 1983, ISBN D-8247-1888-7 (v. 2).

One common characteristic of polyether ionophores is that they are able to complex with monovalent metal ions, such as sodium and potassium, and render such ions organic solvent soluble. These polycyclic ethers enfold a metal ion, forming a loop or ball around the ion with the oxygen function adjacent to the metal and the hydrocarbon backbone forming the exterior of the complex. This three dimensional arrangement, coupled with the fact there is no net charge on the complex, render the whole complex organic solvent soluble. The molecule is able to maintain its loop or ball configuration because of hydrogen bonding between the chemical moieties affixed to opposite ends of the molecule. Usually this involves a carboxylic acid and a hydroxyl group.

The "polyether" nature of the ionophore refers to the considerable number of tetrahydropyrans and tetrahydrofurans found in the ionophore structure. The compounds are characterized by cyclic ether moieties in their chemical structures. Examples include monensin (i.e., A-3823A)

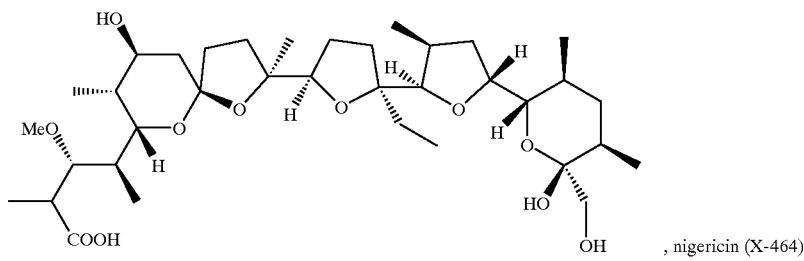

, nigericin (X-464)

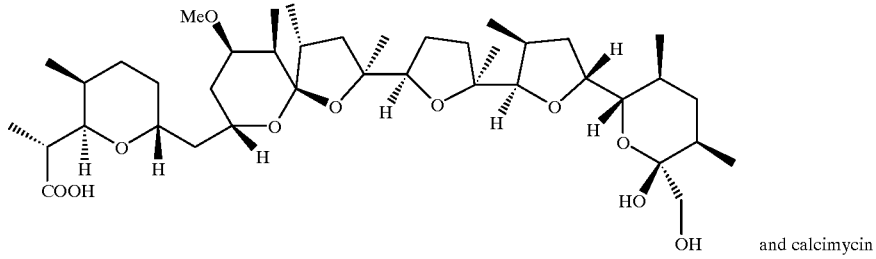

and calcimycin

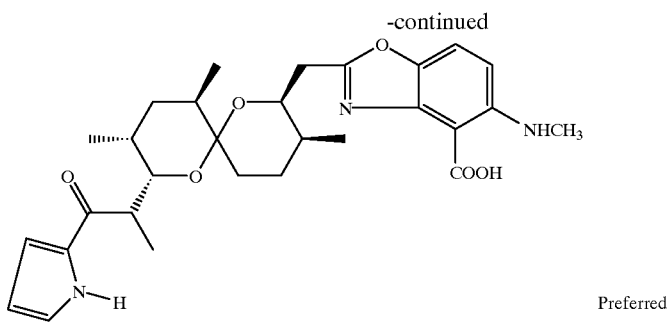

Preferred (i.e., A 23187)
examples include monensin derivatives

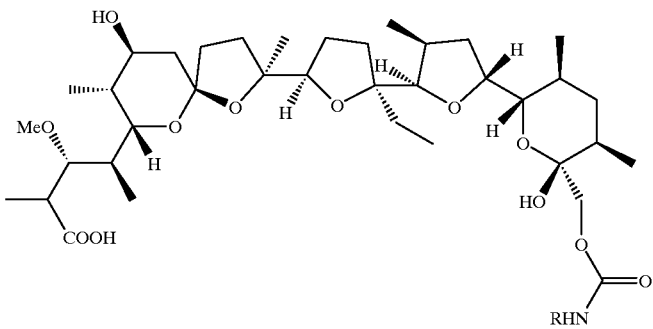

wherein, R is either phenyl, pyridyl or aminoethyl-Fmoc and pharmaceutically acceptable salts or esters thereof.

Cyclic polyether ionophore antibiotics, such as nigericin and monensin, are known to be effective against gram positive type bacteria infections, but have shown reduced or little effectiveness against gram negative type bacterial infections. Generally, such antibiotics have been used primarily in the treatment of non-human bacterial infections. Their preferred use has been in agrochemical applications as an additive to fowl feed stocks for the treatment of coccidiosis (gram-positive) infections of young fowl.

The term "proton pump inhibitor" is art recognized and includes those compounds, e.g., benzimidazoles, which inhibit $H^+$ and $K^+$ ATPase of stomach parietal cells which dose-dependently inhibit the urease activity in *H. pylori*. Suitable examples of PPIs include lansoprazole (2-[[[3-methyl-4-(2,2,2-trifluoroethoxy)-2-pyridyl]methyl]sulfinyl] benzimidazole and omeprazole (5-methoxy-2-[[(4-methoxy-3,5-dimethyl-2-pyridinyl)methyl]sulfinyl]-1H-benzimidazole.

The term "acid blocker or agonist" is art recognized and includes those compounds which slow down the rate of acid secretion into an individual's stomach. Suitable examples include Tagamet® (cimetidine) or Zantac® (rantidine hydrochloride).

The term "acid receptor antagonist" is art recognized and includes those compounds which inhibit the interaction between a receptor site and an agent which binds to the site. Suitable examples include metronidazole (2-methyl-5-nitroimidazole-1-ethanol and clarithromycin (6-O-methylerythromycin).

The term "bismuth salt" is art recognized and includes those compounds which enhance mucus glycoprotein secretion, strengthen viscoelastic gel properties of mucus, cause increased concentration of epithelial growth factor in ulcer tissue and stimulate prostaglandin synthesis in the gastric antral mucosa. A suitable example of a bismuth compound includes tripotassium dicitrato bismuth. An over the counter mixture which contains a bismuth compound is Peptobismal®.

Proton pump inhibitors, acid blockers and bismuth compounds, alone or in combination, can be given in conjunction with polyether ionophore antibiotics or bicyclo spiroethers (described infra) of the invention.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" is art recognized and includes relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1–19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances includes relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyls can be converted into esters via treatment with an esterifying agent such as alkanoyl halides. The term is further intended to include lower hydrocarbon groups capable of being solvated under physiological conditions, e.g., alkyl esters, methyl, ethyl and propyl esters. (See, for example, Berge et al., supra.) A preferred ester group is an acetomethoxy ester group.

When the compounds of the present invention are administered as pharmaceuticals, to humans and mammals, they can be given per se or as a pharmaceutical composition containing, for example, 0.1 to 99.5% (more preferably 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount which controls gram negative bacteria and/or treats a disease state characterized by the presence of a gram negative bacteria, such as *Helicobacter pylori*.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The invention also pertains to a second method for controlling gram negative bacteria in a mammal, e.g., those gram negative bacteria which are agents associated with disorders of the gastrointestinal tract, using a bicyclo spiroether compound. The method includes administering to a mammal a therapeutically effective amount of a bicyclo spiroether compound having at least one heterocyclic moiety attached to at least one of the ether rings to a mammal, such that gram negative bacteria in the mammal is controlled. Preferably, a tetrahydrofuranyl group is attached to a ether ring via a substituted or unsubstituted alkylene diradical.

The term "bicyclo spiroether" is art recognized and is intended to include those ethers having one carbon atom common to both rings. Cyclic ethers useful as a first ring of the bicyclic structure of bicyclo spiroethers include those ethers having a carbon backbone chain of three to twenty carbon atoms, preferably four to seven carbon atoms. Cyclic ethers useful as the second ring of the bicyclo spiroethers includes those having a carbon backbone (methylenes) of three to twenty carbon atoms, preferably four to seven carbon atoms. In a preferred embodiment, both the first and second ring of the bicyclo spiroether are six membered rings (e.g., five carbon atoms in each ring). In another preferred embodiment, a first ring of the bicyclo spiroether is a six membered ring (e.g., five carbon atoms) and the second ring of the bicyclo spiroether is a five membered ring (e.g., four carbon atoms).

It is to be understood that the methylene carbon atoms of both the first and second cyclic ether rings can be each independently substituted at one or more positions with one or two substitutents selected from hydrogen atoms, hydroxyl groups or substituted or unsubstituted alkyl groups.

The term "heterocyclic moiety" is intended to include 3- to 10-membered ring structures, more preferably 4- to 7-membered rings, which ring structures include one to four heteroatoms. Heterocyclic groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylarnino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. A heteroalkyl moiety is an alkyl substituted with a heteroaromatic group.

The term "heteroatom" as used herein means an atom of any element other than carbon or hydrogen. Preferred heteroatoms are nitrogen, oxygen, sulfur and phosphorus.

The term "tetrahyrofuranyl" group is art recognized and is intended to include substituted and unsubstituted tetrahydrofuran groups of the formulae:

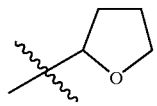

or

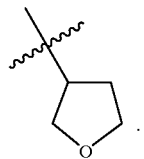

The term "alkylene diradical" is intended to include an organic moiety, such as an aliphatic or aromatic group, which is attached at two positions to two separate organic moieties. Suitable non-limiting examples of alkylene diradicals include

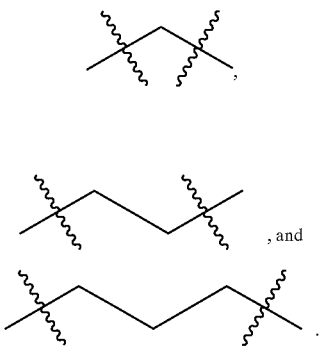

The alkylene diradical can be substituted or unsubstituted with those groups described infra for alkyl and aryl groups.

The invention further pertains to a method for controlling gram negative bacteria in a mammal, e.g., such as gram negative bacteria which are agents associated with disorders of the gastrointestinal tract including compounds having formulae described below. The method includes administering to a mammal a therapeutically effective amount of a compound having the formula:

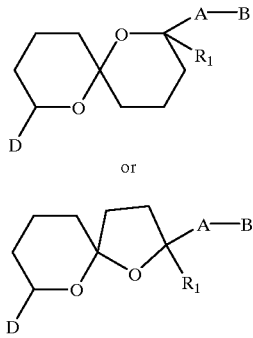

such that gram negative bacteria in the mammal is controlled. $R_1$ is a hydrogen atom or a substituted or unsubstituted alkyl group and A is either a covalent bond connecting the cyclic ring to B or a substituted or unsubstituted alkylene diradical connecting the cyclic ring to B. B is a heterocyclic group, preferably a tetrahydrofuranyl group, and D is a substituted or unsubstituted alkyl group. The methylene carbon atoms of the cyclic rings are each independently substituted at one or more positions with one or two substituents selected from hydrogen atoms, hydroxyl groups or substituted or unsubstituted alkyl groups. The methine carbon atoms are each independently substituted with hydrogen atoms or substituted or unsubstituted alkyl groups.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" refers to unsaturated aliphatic groups analogous in length and possible substitution to the alkyl groups described above, but that contain at least one double bond.

The terms "alkoxyalkyl" and "thioalkoxyalkyl" refer to alkyl groups, as described above, which further include oxygen or sulfur atoms replacing one or more carbons of the hydrocarbon backbone, e.g., catenary oxygen or sulfur atoms.

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls having one to three carbon atoms.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

The term "methine" carbon is art recognized and is intended to include those carbons having a single site for substitution, e.g., by a hydrogen atom or substituted or unsubstituted alkyl groups.

The present invention further pertains to methods for treating a state, e.g., disorder or condition, characterized by the presence of gram negative bacteria in a mammal. An example of such a gram negative bacteria is *Helicobacter pylori*, which is an agent associated with disorders of the gastrointestinal tract of mammals In one embodiment, a method includes administering to a mammal a therapeutically effective amount of a polyether ionophore antibiotic, such that a state characterized by the presence of gram negative bacteria in the mammal is treated.

In another embodiment, a method includes administering to a mammal a therapeutically effective amount of a bicyclo spiroether compound having at least one heterocyclic moiety attached to at least one of the ether rings, such that a state characterized by the presence of gram negative bacteria, such as *Helicobacter pylori* in the mammal is treated. The polyether ionophore antibiotics and bicyclo spiroether compounds of the invention are useful for both prophylactic and/or therapeutic treatments of gram negative bacteria found in the gastrointestinal tract of a mammal.

In still another embodiment, a method includes administering to a mammal a therapeutically effective amount of compound having the formula:

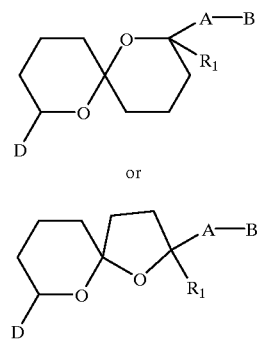

such that a state characterized by the presence of gram negative bacteria, such as *Helicobacter pylori*, in the mammal is treated. A, B, D and $R_1$ are as defined supra.

The language "state characterized by the presence of gram negative bacteria" is intended to include those diseases, disorders or conditions which have been associated with a gram negative bacteria in that the gram negative bacteria is directly or indirectly a causative agent of the disease, disorder or condition. The gram negative bacteria does not have to be the sole causative agent of the disease, disorder or condition merely responsible for causing some of the symptoms typically associated with the disease, disorder, or condition being treated. The gram negative bacteria can be the causative agent alone or at least one other agent can be involved in the state being treated. Examples include ulcers and inflammation and those symptoms not manifested by the presence of ulcerations in the gastric mucosa, such as gastritis, non-ulcer dyspepsia, esophageal reflux disease and peptic ulcer disease; typhus (*Salmonella typhi*), food poisoning (*E. coli* O157:H7), bascillary dysentery (*Shigella dysenteria*), pneumonia ((*Psuedomonas aerugenosa*) and cholera (*Vivrio cholerae*). Preferred examples include those symptoms associated with *Helicobacter pylori*.

The language "treating or treatment of the state characterized by the presence of gram negative bacteria" is intended to include the alleviation of or diminishment of at least one symptom typically associated with the state. The treatment also includes alleviation or diminishment of more than one symptom. Preferably, the treatment cures, e.g., substantially eliminates, the symptoms associated with the state.

The language "therapeutically effective amount" of a polyether ionophore, a bicyclo spiroether compound, or those compounds described supra, is that amount necessary or sufficient to perform its intended function within a mammal, e.g., eradicate or inhibit growth of the gram negative bacteria and/or treat the targeted state. The therapeutically effective amount can vary depending on such factors as the type of gram negative bacteria, the weight of the mammal, or the severity of the symptom(s). One of ordinary skill in the art would be able to study the aforementioned factors and make a determination regarding the effective amount of the compound required without undue experimentation. An in vitro or in vivo assay also can be used to determine an "effective amount" of the compounds described supra. The ordinarily skilled artisan would select an appropriate amount of the compound for use in the aforementioned assay.

The present invention also pertains to methods for controlling *Helicobacter pylori* in a mammal. In one embodiment, a method includes administering to a mammal a therapeutically effective amount of a polyether ionophore antibiotic, such that *Helicobacter pylori* in the mammal is controlled.

In another embodiment, a method includes administering to a mammal a therapeutically effective amount of a bicyclo spiroether compound having at least one heterocyclic moiety attached to at least one of the ether rings, such that *Helicobacter pylori* in the mammal is controlled.

In still another embodiment, a method includes administering to a mammal a therapeutically effective amount of a compound having the formula:

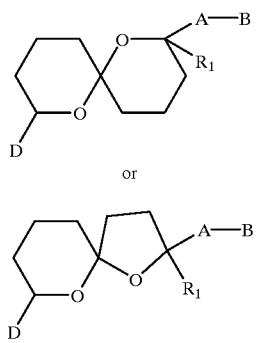

wherein A, B, D and $R_1$ are as defined supra, such that *Helicobacter pylori* in the mammal is controlled.

The present invention further provides methods for treating a gastrointestinal disorder in a mammal characterized by having gram negative bacteria, such as *Helicobacter pylori*, as a causative agent. In one embodiment, a method includes administration of a therapeutically effective amount of a polyether ionophore antibiotic to a mammal, such that a gastrointestinal disorder characterized by having *Helicobacter pylori* as a causative agent is treated.

In another embodiment, a method includes administering to a mammal a therapeutically effective amount of a bicyclo spiroether compound having at least one heterocyclic moiety attached to at least one of the ether rings, such that a gastrointestinal disorder characterized by having *Helicobacter pylori* as a causative agent is treated.

In still another embodiment, a method includes administering to a mammal a therapeutically effective amount of a compound having the formula:

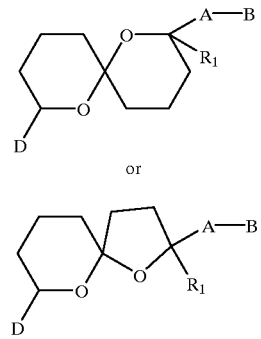

wherein A, B, D and $R_1$ are defined supra, such that a gastrointestinal disorder characterized by having *Helicobacter pylori* as a causative agent is treated.

The phrase "gastrointestinal disorder" is intended to include physical manifestations caused by a foreign stimulus or by gram negative bacteria, e.g., *Helicobacter pylori* in the gastrointestinal tract. Gastrointestinal disorders and can take the form of inflammation or ulceration of a portion of the gastrointestinal tract or gastritis, non-ulcer dyspepsia, esophageal reflux disease and peptic ulcer disease. Preferred examples include those manifestations caused by or associated with *Helicobacter pylori*.

The language "treating a gastrointestinal disorder" is intended to include the alleviation of or diminishment of at least one symptom typically associated with the disorder. The treatment also includes alleviation or diminishment of more than one disorder. Preferably, the treatment cures, e.g., substantially eliminates, the symptoms associated with the disorder, e.g. inflammation, ulceration, gastritis, etc.

The language "therapeutically effective amount" of a polyether ionophore, a bicyclo spiroether compound, or those compounds described supra, is that amount necessary or sufficient to perform its intended function within a mammal, e.g., reduce, inhibit or eliminate symptoms associated with a gastrointestinal disorder as a result of the presence of a gram negative bacteria, such as *Helicobacter pylori*, in the mammal. The therapeutically effective amount can vary depending on such factors as the amount of gram negative bacteria present, the weight of the mammal, or the severity of the disorder(s). One of ordinary skill in the art would be able to study the aforementioned factors and make a determination regarding the effective amount of the compound required without undue experimentation.

The present invention also provides methods for treating an ulcer in the gastrointestinal tract of a mammal. In one embodiment, the method includes administration of a therapeutically effective amount of a polyether ionophore antibiotic to a mammal, such that an ulcer of the gastrointestinal tract of the mammal is treated.

The present invention also provides methods for treating an ulcer associated with *Helicobacter pylori* in a mammal. In one embodiment, a method includes administering to a mammal a therapeutically effective amount of a polyether ionophore antibiotic, such that an ulcer associated with *Helicobacter pylori* in the mammal is treated.

In another embodiment, a method includes administering to a mammal a therapeutically effective amount of a bicyclo spiroether compound having at least one heterocyclic moiety attached to at least one of the ether rings, such that an ulcer associated with *Helicobacter pylori* in the mammal is treated.

In still another embodiment, the method includes administering to a mammal a therapeutically effective amount of a compound having the formula:

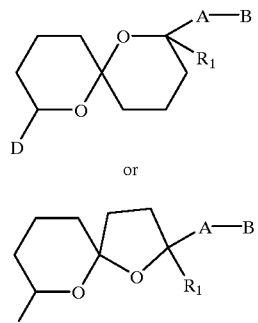

or wherein A, B, D and $R_1$ are defined supra, such that an ulcer associated with *Helicobacter pylori* in the mammal is treated.

The term "ulcer" is art recognized and is intended to breaks in the skin or mucous membrane with loss of surface tissue, e.g. degradation of the lining of the esophagus, stomach lining, and/or lining of the small and/or large intestine. Ulcers, such as peptic ulcers, can be caused by gram negative bacteria such as *Helicobacter pylori*.

The language "an ulcer associated with *Helicobacter pylori*" is intended to include ulcers, inflammation, and/or erosion of the gastrointestinal lining which causes discomfort to the mammal and is associated directly or indirectly with the presence of *Helicobacter pylori* in the mammal.

The language "treating an ulcer associated with *Helicobacter pylori*" is intended to include the alleviation of or diminishment of at least one symptom typically associated with an ulcer associated with *Helicobacter pylori*. The treatment also includes alleviation or diminishment of more than one symptom. Preferably, the treatment cures, e.g., substantially eliminates, the symptoms associated with the ulcer.

The language "therapeutically effective amount" of a polyether ionophore, a bicyclo spiroether compound, or those compounds described supra, is that amount necessary or sufficient to perform its intended function within a mammal, e.g., reduce, inhibit or eliminate symptoms associated with an ulcer as a result of the presence of *Helicobacter pylori* in the mammal. The therapeutically effective amount can vary depending on such factors as the amount of *Helicobacter pylori* present, the weight of the mammal, or the severity of the symptom(s). One of ordinary skill in the art would be able to study the aforementioned factors and make a determination regarding the effective amount of the compound required without undue experimentation.

The present invention pertains to a packaged pharmaceutical composition for controlling gram negative bacteria. The container holds a therapeutically effective amount of a pharmaceutical composition for controlling gram negative bacteria and instructions for using the pharmaceutical composition for control of the gram negative bacteria. The pharmaceutical composition includes at least one polyether ionophore antibiotic, such that gram negative bacteria is controlled. Polyether ionophore antibiotics include monensin, nigericin and calcimycin and pharmaceutically acceptable salts or esters thereof. Preferred polyether ionophore antibiotics include compounds

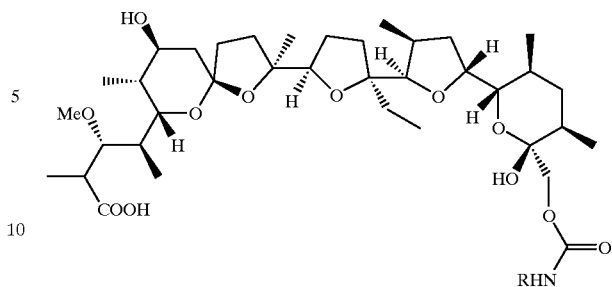

having the formula
wherein, R is either phenyl, pyridyl or aminoethyl-Fmoc and pharmaceutically acceptable salts and esters thereof.

The invention is further illustrated by the following examples which in no way should be construed as being further limiting. The contents of all references, pending patent applications and published patent applications, cited throughout this application are hereby incorporated by reference. It should be understood that the in vitro assays and/or correlated animal models used throughout the examples are accepted models and that the demonstration of efficacy in these models is predictive of efficacy in humans.

EXEMPLIFICATION

Synthesis of Monensin Derivatives

Synthesis of Monensin Benzyl Ester

Monensin sodium salt (1.0 g, 1.4 mmol) in acetonitrile (20 ml) was treated with diazabicyclo [2.2.2] octane (0.3 g, 2.7 mmol) followed by benzyl bromide (2 g, 11.7 mmol) and cryptand [2.2.2]. The reaction mixture was stirred at room temperature with exclusion of light for 14 days. After 10 days an additional quantity of benzyl bromide (2 g, 11.7 mmol) was added. The solvent was evaporated and the crude product redissolved in dichloromethane, washed with deionized water and dried over magnesium sulfate. The crude product was chromatographed on silica gel eluting with hexane-ethyl acetate gradient. Excess benzyl bromide eluted from the column first followed by benzylmonensin which was isolated as a colorless oil after removal of the solvent (280 mg, 26%), (MS, positive ion ESI showed 783 peak; calc. for sodiated product 783). This compound has been reported previously (Tsukube J. Org. Chem. 56, 875, 1991).

Synthesis of 26-O-arylcarbamoylmonensins

These compounds were prepared using a modification of the procedure described by Westley and co-workers for the synthesis of the 26-O-carbamoylmonensins. (Westley, et al., Antibiotics 34, 1195, 1983).

26-O Phenylmonensin

A solution of monensin (400 mg, 0.6 mmol) in dry toluene (2 ml) was treated with phenylisocyanate (71 mg, 0.6 mmol) and the reaction mixture stirred at ambient temperature with exclusion of light for 24 h. The toluene was evaporated under reduced pressure and crude product purified by column chromatography on silica gel eluting with hexane-ethyl acetate gradient. A major UV-active band, which had a higher $R_1$ value than residual monensin, was evaporated to give a white crystalline solid 130 mg, 27% (MS, positive ion ESI showed 811 peak; calc mass for sodiated adduct of product 811).

26-O-(3-pyridylcarbamoyl) Monensin 3-pyridylcarbamoyl monensin compound was prepared as above in 20% yield by reaction of monensin with 3-pyridylisocyanate (A. Orahovats Helv. Chimica Acata 70, 262, 1987) followed by chromatography as described above. (MS, negative ion ESI showed 789 peak; calc mass 790).

26-O-[1-(Fmoc-amino) Ethylcarbamoyl] Monensin

Fmoc-amino ethylcarbamoyl monensin was prepared as above in 35% yield by reaction of monensin with 1-(Fmoc-amino) ethylisocyanate followed by column chromatography on silica eluting with ethyl acetate and 5% methanol in ethylacetate. (MS, negative ion ESI showed 977 peak; calc mass 978).

Minimum Inhibitory Concentration (MIC) of Monensin and Nigericin against *H. pylon*

Drug Preparation

Monensin (Sigma Cat. No. M-5273) was dissolved in 100% absolute ethanol (AAPER Alcohol and Chemical Co.) at a concentration of 20 mg/ml. Subsequent dilutions were made in ethanol immediately prior to use. Nigericin (Sigma Cat. No. N-7143) was dissolved in DMSO at 2 mg/ml. Subsequent dilutions were made in BHI medium (Brain heart infusion broth, Difco # 0037-07-0) immediately prior to use.

| Initial Concentration | Final Concentrations (1:200) |
|---|---|
| 2 mg/ml | 10 μg/ml |
| 200 μg/ml | 1 μg/ml |
| 20 μg/ml | 0.1 μg/ml |
| 2 μ/ml | 10 ng/ml |
| 200 ng/ml | 1 ng/ml |
| 20 ng/ml | 0.1 ng/ml |

Media Preparation

Blood agar base (BAB) was prepared containing 1.5% agar and autoclaved. 20 ml samples of autoclaved BAB were poured into 50 mL tubes and placed in a 56° C. water bath.

Plate Preparation

100 μl of a drug (final concentration equivalent to 1:200 of original concentration) and 1.2 ml of sheep blood (Colorado Serum Company # CS-112) (blood diluted in a 1:1 buffer providing a 3% concentration of blood per 20 ml medium sample) were added to 20 ml sample of media and mixed. The mixed media preparation was poured into a petri dished and allowed to solidify.

Organism Preparation

Prior to inoculation of petri plates, bacteria or cultures were examined for morphology under a phase microscope to confirm motility and physical characteristics, e.g., spiral shaped. The organisms were washed off the plate into PBS (Phosphate buffered saline) (80.0 g NaCl, 2.0 g KCl, 2.4 g $KH_2PO_4$ 11.5 g $Na_2HPO_4$ or 24.4 g $Na_2HPO_4/2H_2O$ per 1 liter deionized water, pH 7.2, sterilized by autoclaving) and diluted into BHI at a concentration of $10^8$/ml (O.D. of 0.3 units diluted 1:30). Ten microliters of solution containing $10^6$ organisms were spread onto a petri plate and grown under microaerophilic conditions for 3 days unless specified. Control organisms were grown under microaerophilic conditions.

Results

Inhibition of growth was determined by the amount of colonies present within the petri plate. The following factors were used for growth inhibition: ±=0–20 colonies, +=20–50 colonies, ++=50–200 colonies and +++=200+ colonies.

Table I
*H. pylori* ATCC 43504
Controls:
   Organisms+0.5% DMSO No growth
   Organisms+0.05% DMSO (+++)
   Organisms without DMSO (+++)
A stock solution containing 10 μg/ml of therapeutic compound and 0.5% DMSO was prepared for each therapeutic compound. Serial dilutions were prepared from each stock solution.

| Final drug Concentration | Monensin | Nigericin |
|---|---|---|
| 10 μg/ml | No growth | No growth |
| 1 μg/ml | No growth | No growth |
| 100 ng/ml | No growth | (++) |
| 10 ng/ml | (+) | (+++) |
| 1 ng/ml | (+) | (+++) |
| 0.1 ng/ml | (+++) | (+++) |

Table II
*H. pylori* (Urease Positive) ATCC 43504
Controls:
   Organisms+0.5% DMSO (+++)
   Organisms+0.05% DMSO (+++)
   Organisms without DMSO (+++)
A stock solution containing 10 μg/ml of therapeutic compound and 0.5% DMSO was prepared for each therapeutic compound. Serial dilutions were prepared from each stock solution.

| Final drug Concentration | Monensin | Nigericin |
|---|---|---|
| 10 μg/ml | No growth | No growth |
| 1 μg/ml | +/− | No growth |
| 100 ng/ml | (+++) | |
| 10 ng/ml | | (+++) |
| 1 ng/ml | (+++) | (+++) |
| 0.1 ng/ml | (+++) | (+++) |

Table III
*H. pylori* (Urease Negative) (Wild Strain of ATCC 43504)
Controls:
   Organisms+0.5% DMSO (+++)
   Organisms+0.05% DMSO (+++)
   Organisms without DMSO (+++)
A stock solution containing 10 μg/ml of therapeutic compound and 0.5% DMSO was prepared for each therapeutic compound. Serial dilutions were prepared from each stock solution.

| Final drug Concentration | Monensin | Nigericin |
|---|---|---|
| 10 μg/ml | No growth | No growth |
| 1 μg/ml | No growth | No growth |
| 100 ng/ml | (+++) | (+++) |
| 10 ng/ml | (+++) | (+++) |
| 1 ng/ml | (+++) | |
| 0.1 ng/ml | (+++) | (+++) |

Table IV

*H. pylori* (Urease Positive) ATCC 43504

Controls:

Organisms+0.5% DMSO (+++)

Organisms+0.05% DMSO (+++)

Organisms without DMSO (+++)

A stock solution containing 10 μg/ml of therapeutic compound and 0.5% DMSO was prepared for each therapeutic compound. Serial dilutions were prepared from each stock solution.

| Final drug Concentration | Monensin | Nigericin |
|---|---|---|
| 10 μg/ml | No growth | No growth |
| 1 μg/ml | No growth | No growth |
| 100 ng/ml | (+++) | (+++) |
| 10 ng/ml | (+++) | (+++) |
| 1 ng/ml | (+++) | (+++) |
| 0.1 ng/ml | (+++) | (+++) |

Table V

*H. pylori* ATCC 43504

Controls:

Organisms+0.5% DMSO (+++)

Organisms+0.05% DMSO (+++)

Organisms without DMSO (+++)

A stock solution containing 10 μg/ml of therapeutic compound and 0.5% DMSO was prepared for each therapeutic compound. Serial dilutions were prepared from each stock solution.

Assay done in the presence of 10 mM urea which was added to and mixed with the culture medium prior to pouring into culture plates.

| Final drug Concentration | Monensin | Nigericin |
|---|---|---|
| 10 μg/ml | No growth | No growth[1] |
| 1 μg/ml | No growth | (±)[1] |
| 100 ng/ml | (+++) | (+++)[1] |
| 10 ng/ml | (+++) | (++)[1] |
| 1 ng/ml | (+++) | (+++)[1] |
| 0.1 ng/ml | (+++) | (+++)[1] |

[1]assay done in duplicate

Table VI

*H. pylori* ATCC 43504

Control:

Organisms+0.05% DMSO (+++)

Organisms without DMSO (+++)

A stock solution containing 1 μg/ml of therapeutic compound and 0.05% DMSO was prepared for each therapeutic compound. Serial dilutions were prepared from each stock solution.

Assay done in the presence of 2.5 mM urea prepared as above at a lower concentration of urea.

| Final drug Concentration | Monensin | Nigericin |
|---|---|---|
| 1 μg/ml | No growth | (±) |
| 10 ng/ml | (+++) | (+++) |
| 1 ng/ml | (+++) | (+++) |

Table VII

*H. pylori* (Urease Positive) ATCC 43504

Controls:

Organisms+0.5% DMSO (+++)

Organisms+0.05% DMSO (+++)

Organisms without DMSO (+++)

A stock solution containing 10 μg/ml of therapeutic compound and 0.5% DMSO was prepared for each therapeutic compound. Serial dilutions were prepared from each stock solution.

| Final drug Concentration | Lasalocid | Salinomycin | Inomycin | A23187 |
|---|---|---|---|---|
| 10 μg/ml | (+++) | No growth | (+++) | No growth |
| 1 μg/ml | (+++) | (+++) | (+++) | No growth |
| 100 ng/ml | (+++) | (+++) | (+++) | (+++) |
| 10 ng/ml | (+++) | (+++) | (+++) | (+++) |
| 1 ng/ml | (+++) | (+++) | (+++) | (+++) |
| 0.1 ng/ml | (+++) | (+++) | (+++) | (+++) |

Table VIII

*H. pylori* (Urease Positive) ATCC Number 51652

Controls:

Organisms+0.5% ethanol (+++)

Organisms without ethanol (+++)

A stock solution containing 100 μg/ml of therapeutic compound and 0.5% DMSO was prepared for each therapeutic compound. Serial dilutions were prepared from each stock solution.

| | Final drug concentration | Monensin |
|---|---|---|
| 1. | 100 μg/ml | No growth |
| 2. | 50 μg/ml | No growth |
| 3. | 25 μg/ml | No growth |
| 4. | 12.5 μg/ml | No growth |
| 5. | 6.25 μg/ml | No growth |
| 6. | 3.125 μg/ml | No growth |
| 7. | 1.56 μg/ml | No growth |
| 8. | 0.78 μg/ml | No growth |
| 9. | 0.39 μg/ml | No growth |
| 10. | 0.195 μg/ml | No growth |
| 11. | 0.098 μg/ml | No growth |

Table IX

*H. pylori* ATCC 43504

Controls:

Organisms+0.5% ethanol (+++)

Organisms without ethanol (+++)

A stock solution containing 100 μg/ml of therapeutic compound and 0.5% DMSO was prepared for each therapeutic compound. Serial dilutions were prepared from each stock solution.

| Final drug concentration | | Fmoc-Ala-monensin |
|---|---|---|
| 1. | 100 μg/ml | No growth |
| 2. | 50 μg/ml | No growth |
| 3. | 25 μg/ml | No growth |
| 4. | 12.5 μg/ml | No growth |
| 5. | 6.25 μg/ml | (±) |
| 6. | 3.125 μg/ml | (+++) |
| 7. | 1.56 μg/ml | (+++) |
| 8. | 0.78 μg/ml | (+++) |
| 9. | 0.39 μg/ml | (+++) |
| 10. | 0.195 μg/ml | (+++) |
| 11. | 0.098 μg/ml | (+++) |

MIC = 6.25 μg/ml

Table X

*H. pylori* ATCC 43504
Controls:

Organisms+0.5% ethanol (+++)

Organisms without ethanol (+++)

A stock solution containing 100 μg/ml of therapeutic compound and 0.5% DMSO was prepared for each therapeutic compound. Serial dilutions were prepared from each stock solution.

| Final drug concentration | | Monensin phenyl carbamate |
|---|---|---|
| 1. | 100 μg/ml | No growth |
| 2. | 50 μg/ml | No growth |
| 3. | 25 μg/ml | No growth |
| 4. | 12.5 μg/ml | No growth |
| 5. | 6.25 μg/ml | No growth |
| 6. | 3.125 μg/ml | (±) few small colonies |
| 7. | 1.56 μg/ml | (+) small colonies |
| 8. | 0.78 μg/ml | (++) |
| 9. | 0.39 μg/ml | (++) |
| 10. | 0.195 μg/ml | (+++) |
| 11. | 0.098 μg/ml | (+++) |

MIC = 1.56 μg/ml

Table XI

*H. pylori* ATCC 43504
Controls:

Organisms+0.5% ethanol (+++)

Organisms without ethanol (+++)

A stock solution containing 100 μg/ml of therapeutic compound and 0.5% DMSO was prepared for each therapeutic compound. Serial dilutions were prepared from each stock solution.

| Final drug concentration | | Monensin phenyl carbamate |
|---|---|---|
| 1. | 100 μg/ml | No growth |
| 2. | 50 μg/ml | No growth |
| 3. | 25 μg/ml | No growth |
| 4. | 12.5 μg/ml | No growth |
| 5. | 6.25 μg/ml | No growth |
| 6. | 3.125 μg/ml | (±) |
| 7. | 1.56 μg/ml | (++) |
| 8. | 0.78 μg/ml | (+++) |
| 9. | 0.39 μg/ml | (+++) |
| 10. | 0.195 μg/ml | (+++) |
| 11. | 0.098 μg/ml | (+++) |

MIC = 3.12 μg/ml

Table XII

*H. pylori* ATCC 43504
Controls:

Organisms+0.5% ethanol (+++)

Organisms without ethanol (+++)

A stock solution containing 100 μg/ml of therapeutic compound and 0.5% DMSO was prepared for each therapeutic compound. Serial dilutions were prepared from each stock solution.

| Final drug concentration | | Benzyl Monensis |
|---|---|---|
| 1. | 100 μg/ml | (±) |
| 2. | 50 μg/ml | (±) |
| 3. | 25 μg/ml | (±) |
| 4. | 12.5 μg/ml | (++) |
| 5. | 6.25 μg/ml | (+++) |
| 6. | 3.125 μg/ml | (+++) |
| 7. | 1.56 μg/ml | (+++) |
| 8. | 0.78 μg/ml | (+++) |
| 9. | 0.39 μg/ml | (+++) |
| 10. | 0.195 μg/ml | (+++) |
| 11. | 0.098 μg/ml | (+++) |

MIC = 25 μg/ml

Table XIII

*H. pylori* ATCC 43504
Controls:

Organisms+0.5% ethanol (+++)

Organisms without ethanol (+++)

A stock solution containing 100 μg/ml of therapeutic compound and 0.5% DMSO was prepared for each therapeutic compound. Serial dilutions were prepared from each stock solution.

| Final drug concentration | | Monensin |
|---|---|---|
| 1. | 100 μg/ml | No growth |
| 2. | 50 μg/ml | No growth |
| 3. | 25 μg/ml | No growth |
| 4. | 12.5 μg/ml | No growth |
| 5. | 6.25 μg/ml | No growth |
| 8. | 0.78 μg/ml | No growth |
| 9. | 0.39 μg/ml | (±) |
| 10. | 0.195 μg/ml | (++) |
| 11. | 0.098 μg/ml | (+++) |

MIC = 0.39 μg/ml

Table XIV

Staph ATCC 14775
Controls:

Organisms+0.5% DMSO (+++)

Organisms+0.05% DMSO (+++)

Organisms without DMSO (+++)

A stock solution containing 10 μg/ml of therapeutic compound and 0.5% DMSO was prepared for each therapeutic compound. Serial dilutions were prepared from each stock solution.

| | Non-microaerophilic conditions | |
|---|---|---|
| Final drug Concentration | Monensin | Nigericin |
| 10 µg/ml | No growth | No growth |
| 1 µg/ml | (+++***) | No growth |
| 100 ng/ml | (+++) | (+++***) |
| 10 ng/ml | (+++) | (+++) |
| 1 ng/ml | (+++) | (+++) |
| 0.1 ng/ml | (+++) | (+++) |

***good growth, but the colonies are smaller than in controls.

Table XV
Staph. ATCC 14775
Controls:
   Organisms+0.5% DMSO (+++)
   Organisms+0.05% DMSO (+++)
   Organisms without DMSO (+++)
A stock solution containing 10 µg/ml of therapeutic compound and 0.5% DMSO was prepared for each therapeutic compound. Serial dilutions were prepared from each stock solution.

| | Non microaerophilic conditions | |
|---|---|---|
| Final drug concentration | Lasalocid | Salinomycin |
| 10 µg/ml | No growth | No growth |
| 1 µg/ml | (+++) | (+++)¹ |
| 100 ng/ml | (+++) | (+++) |
| 10 ng/ml | (+++) | (+++) |

¹small colonies

Table XVI
Staph. ATCC 14775
Controls:
   Organisms+0.5% ethanol (+++)
   Organisms+0.25% ethanol (+++
   Organisms+0.125% ethanol (+++)
   Organisms without ethanol (+++)
A stock solution containing 100 µg/ml of therapeutic compound and 0.5% DMSO was prepared for each therapeutic compound. Serial dilutions were prepared from each stock solution.

| | Non-aerophilic conditions. | |
|---|---|---|
| | Final drug concentration | Monensin |
| 1. | 100 µg/ml | No growth |
| 2. | 50 µg/ml | No growth |
| 3. | 25 µg/ml | (±)¹ |
| 4. | 12.5 µg/ml | (±)¹ |
| 5. | 6.25 µg/ml | (+)² |
| 6. | 3.125 µg/ml | (+)² |
| 7. | 1.56 µg/ml | (+)² |
| 8. | 0.78 µg/ml | (++) |
| 9. | 0.39 µg/ml | (+++) |
| 10. | 0.195 µg/ml | (+++) |
| 11. | 0.098 µg/ml | (+++) |

(±)¹ = very small colonies, (+)² = small colonies

Table XVII
H. pylori (Urease Positive) ATCC Number 51652
Assay Done in Blood Agar Base+3% Sheep Blood Controls:
   Organisms+0.5% DMSO (+++)
   Organisms+0.05% DMSO (+++)
   Organisms without DMSO (+++)
A stock solution containing 10 µg/ml of therapeutic compound and 0.5% DMSO was prepared for each therapeutic compounds Serial dilutions were prepared from each stock solution.

| | Lasalocid | Salinomycin |
|---|---|---|
| 10 µg/ml | (+++) | No growth |
| 1 µg/ml | (+++) | (+++) |
| 100 ng/ml | (+++) | (+++) |
| 10 ng/ml | (+++) | (+++) |
| 1 ng/ml | (+++) | (+++) |
| 0.1 ng/ml | (+++) | (+++) |
| Final drug Concentration | Ionomycin | A23187 |
| 10 µg/ml* | (+++) | No growth |
| 1 µg/ml** | (+++) | No growth |
| 100 ng/ml | (+++) | (+++) |
| 10 ng/ml | (+++) | (+++) |
| 1 ng/ml | (+++) | (+++) |
| 0.1 ng/ml | (+++) | (+++) |

As is clear from the data presented above, several polyether ionophore antibiotics provide a method for treatment of human gastric *H. pylori* infections. These same antibiotics have little if any effect on gram positive bacteria.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for controlling gram negative bacteria in a human, comprising administering to a human a therapeutically effective amount of a bicyclo spiroether compound having at least one heterocyclic moiety attached to at least one of the ether rings, such that gram negative bacteria in the human is controlled.

2. The method of claim 1, wherein both ether rings are six membered rings.

3. The method of claim 1, wherein one ether ring is a six membered ring and one ether ring is five membered.

4. The method of claim 1, wherein at least one heterocyclic moiety is directly attached to one of the ether rings.

5. The method of claim 4, wherein said heterocyclic moiety is a tetrahydrofuranyl group.

6. The method of claim 1, wherein at least one heterocyclic moiety is attached to one of the ether rings via a substituted or unsubstituted alkylene diradical.

7. The method of claim 6, wherein said heterocyclic moiety is a tetrahydrofuranyl group.

8. The method of claim 1, wherein said gram negative bacteria is an agent associated with disorders of the gastrointestinal tract.

9. The method of claim 8, wherein said gram negative bacteria is *Helicobacter pylori*.

10. The method of claim 1, further comprising administering a proton pump inhibitor, an acid agonist or blocker, a bismuth salt or combinations thereof in combination with said polyether ionophore antibiotic.

11. A method for treating a state characterized by the presence of gram negative bacteria in a human, comprising administering to a human a therapeutically effective amount of a bicyclo spiroether compound having at least one heterocyclic moiety attached to at least one of the ether rings, such that a state characterized by the presence of gram negative bacteria in the human is treated.

12. The method of claim 11, wherein both ether rings are six membered rings.

13. The method of claim 11, wherein one ether ring is a six membered ring and one ether ring is five membered.

14. The method of claim 11, wherein at least one heterocyclic moiety is directly attached to one of the ether rings.

15. The method of claim 14, wherein said heterocyclic moiety is a tetrahydrofuranyl group.

16. The method of claim 11, wherein at least one heterocyclic moiety is attached to one of the ether rings via a substituted or unsubstituted alkylene diradical.

17. The method of claim 16, wherein said heterocyclic moiety is a tetrahydrofuranyl group.

18. The method of claim 11, wherein the gram negative bacteria is an agent associated with disorders of the gastrointestinal tract.

19. The method of claim 11, wherein said gram negative bacteria is *Helicobacter pylori*.

20. The method of claim 11, further comprising administering a proton pump inhibitor, an acid agonist or blocker, a bismuth salt or combinations thereof in combination with said polyether ionophore antibiotic.

* * * * *